United States Patent
Iketani

(10) Patent No.: US 8,451,327 B2
(45) Date of Patent: May 28, 2013

(54) ELECTRONIC ENDOSCOPE, ENDOSCOPE LIGHT UNIT, ENDOSCOPE PROCESSOR, AND ELECTRONIC ENDOSCOPE SYSTEM

(75) Inventor: Kohei Iketani, Saitama (JP)

(73) Assignee: Hoya Corporation, Tokyo (JP)

( * ) Notice: Subject to any disclaimer, the term of this patent is extended or adjusted under 35 U.S.C. 154(b) by 2022 days.

(21) Appl. No.: 11/464,505

(22) Filed: Aug. 15, 2006

(65) Prior Publication Data

US 2007/0040906 A1 Feb. 22, 2007

(30) Foreign Application Priority Data

Aug. 18, 2005 (JP) ................................. 2005-237392
Aug. 22, 2005 (JP) ................................. 2005-239946

(51) Int. Cl.
*H04N 7/18* (2006.01)
*A62B 1/04* (2006.01)
*A61B 1/04* (2006.01)
*A61B 1/06* (2006.01)

(52) U.S. Cl.
USPC ................................. 348/65; 348/69; 348/70

(58) Field of Classification Search
USPC ........................................................ 348/65
See application file for complete search history.

(56) References Cited

U.S. PATENT DOCUMENTS

| | | | | |
|---|---|---|---|---|
| 4,951,135 A | * | 8/1990 | Sasagawa et al. | 348/69 |
| 4,961,110 A | * | 10/1990 | Nakamura | 348/70 |
| 5,590,660 A | | 1/1997 | MacAulay et al. | |
| 5,827,190 A | | 10/1998 | Palcic et al. | |
| 6,686,949 B2 | | 2/2004 | Kobayashi et al. | |
| 6,697,101 B1 | | 2/2004 | Takahashi et al. | |
| 6,858,004 B1 | | 2/2005 | Ozawa et al. | |
| 6,945,928 B2 | | 9/2005 | Kobayashi et al. | |
| 2002/0014595 A1 | | 2/2002 | Sendai et al. | |
| 2003/0176768 A1 | | 9/2003 | Gono et al. | |
| 2005/0104989 A1 | | 5/2005 | Shizukuishi | |

FOREIGN PATENT DOCUMENTS

| | | |
|---|---|---|
| JP | 04-357926 | 12/1992 |
| JP | 5-228109 | 9/1993 |
| JP | 6-054792 | 3/1994 |
| JP | 10-500588 | 1/1998 |

(Continued)

OTHER PUBLICATIONS

Japan Office action, dated Dec. 21, 2010 along with an english translation thereof.

(Continued)

*Primary Examiner* — Christopher S Kelley
*Assistant Examiner* — Hee-Yong Kim
(74) *Attorney, Agent, or Firm* — Greenblum & Bernstein, P.L.C.

(57) ABSTRACT

An endoscope system comprising an imaging device, an input block, and a signal processing block, is provided. The imaging device has first, second, third, and fourth pixels. The first, second, third, and fourth pixels are covered with first, second, third, and fourth color filters, respectively. The first, second, third, and fourth color filters can be penetrated by first, second, third, and fourth light components, respectively. The first light component reaches a depth, predetermined according to the location of an object, under an organ. The second light component belongs to an identified color of the first light component. Further, a band of the second light component is different from that of the first light component. The input block detects a user's input for selecting one of a number of predetermined display modes. The signal processing block carries out edge enhancement processing for a pixel signal generated by the first pixel. The edge enhancement processing for the pixel signal is carried out when a narrow band image display mode is selected.

11 Claims, 5 Drawing Sheets

FOREIGN PATENT DOCUMENTS

| | | |
|---|---|---|
| JP | 10-201707 | 8/1998 |
| JP | 10-309282 | 11/1998 |
| JP | 11-104061 | 4/1999 |
| JP | 2002-045330 | 2/2002 |
| JP | 2002-095635 | 4/2002 |
| JP | 2002-271804 | 9/2002 |
| JP | 2002-330919 | 11/2002 |
| JP | 2003-018467 | 1/2003 |
| JP | 2003-087806 | 3/2003 |
| JP | 2003-093336 | 4/2003 |
| JP | 2003-153850 | 5/2003 |
| JP | 2004-24497 | 1/2004 |
| JP | 2004-258497 | 9/2004 |
| JP | 2005-151077 | 6/2005 |
| JP | 2005-198794 | 7/2005 |
| WO | 2007/010709 | 1/2007 |

OTHER PUBLICATIONS

Japan Office action, dated Nov. 16, 2010 along with an english translation thereof.

English Language Abstract of JP 2005-198794.

U.S. Appl. No. 11/464,531 to Iketani, filed Aug. 15, 2006.

* cited by examiner

ELECTRONIC ENDOSCOPE, ENDOSCOPE LIGHT UNIT, ENDOSCOPE PROCESSOR, AND ELECTRONIC ENDOSCOPE SYSTEM

BACKGROUND OF THE INVENTION

1. Field of the Invention

The present invention relates to an endoscope system that captures an organ image and displays the captured image.

2. Description of the Related Art

It is known that the depth that light reaches under an organ depends on the wavelength of the light. As shown in FIG. 6, when light of a shorter wavelength is irradiated onto an organ and reaches a shallower area under the organ, then the intensity of the reflected light of a tissue located in a shallow area under the organ is relatively strong (referred to as "Ts" in FIG. 6). On the other hand, when light of a longer wavelength reaches a deeper area under the organ, then the intensity of the reflected light of a tissue located in a deep area under the organ is relatively strong (referred to as "Td" in FIG. 6).

When light of a shorter wavelength within a narrow band of short length is irradiated onto an organ, a tissue located in a shallow area under the organ, such as a capillary, may be clearly displayed. An endoscope system that can capture an image of a tissue under the organ is proposed to take advantage of the above property. However, such an endoscope system normally forms a complicated structure, such as a field sequential image pickup system.

SUMMARY OF THE INVENTION

Therefore, an object of the present invention is to provide an electronic endoscope, an endoscope light system, endoscope processor, and an electronic endoscope system that enable an image of tissue under an organ to be captured and displayed without using a complicated structure.

According to the present invention, an electronic endoscope comprising an imaging device is provided. The imaging device has a first pixel. The first pixel is covered with a first color filter. The first color filter is penetrated by a first light component. The first light component reaches a depth, predetermined according to the location of an object, under an organ.

Further, a wavelength of the first light component is within a band between 400 nm and 450 nm.

According to the present invention, an endoscope light unit comprising a light source, a light source filter, and a filter driving unit is provided. The light source emits illumination light to illuminate an object. The light source filter shields a light component within a band of a predetermined wavelength from the illumination light. The filter driving unit inserts the light source filter into an optical path of the illumination light. Alternatively, the filter driving unit removes the light source filter from the optical path.

Further, the light component, of which the wavelength is shorter than 550 nm, can penetrate the light source filter.

According to the present invention, an endoscope processor comprising an input block and a signal processing block is provided. The input block detects a user's input for selecting one of a number of predetermined display modes. The signal processing block carries out edge enhancement processing only for a pixel signal generated by the first pixel. The edge enhancement process for the pixel signal is carried out only when a narrow band image display mode is selected. The narrow band image display mode is one of the predetermined display modes.

BRIEF DESCRIPTION OF THE DRAWINGS

The objects and advantages of the present invention may be better understood from the following description, with reference to the accompanying drawings in which.

DESCRIPTION OF THE PREFERRED EMBODIMENTS

Figure 1:
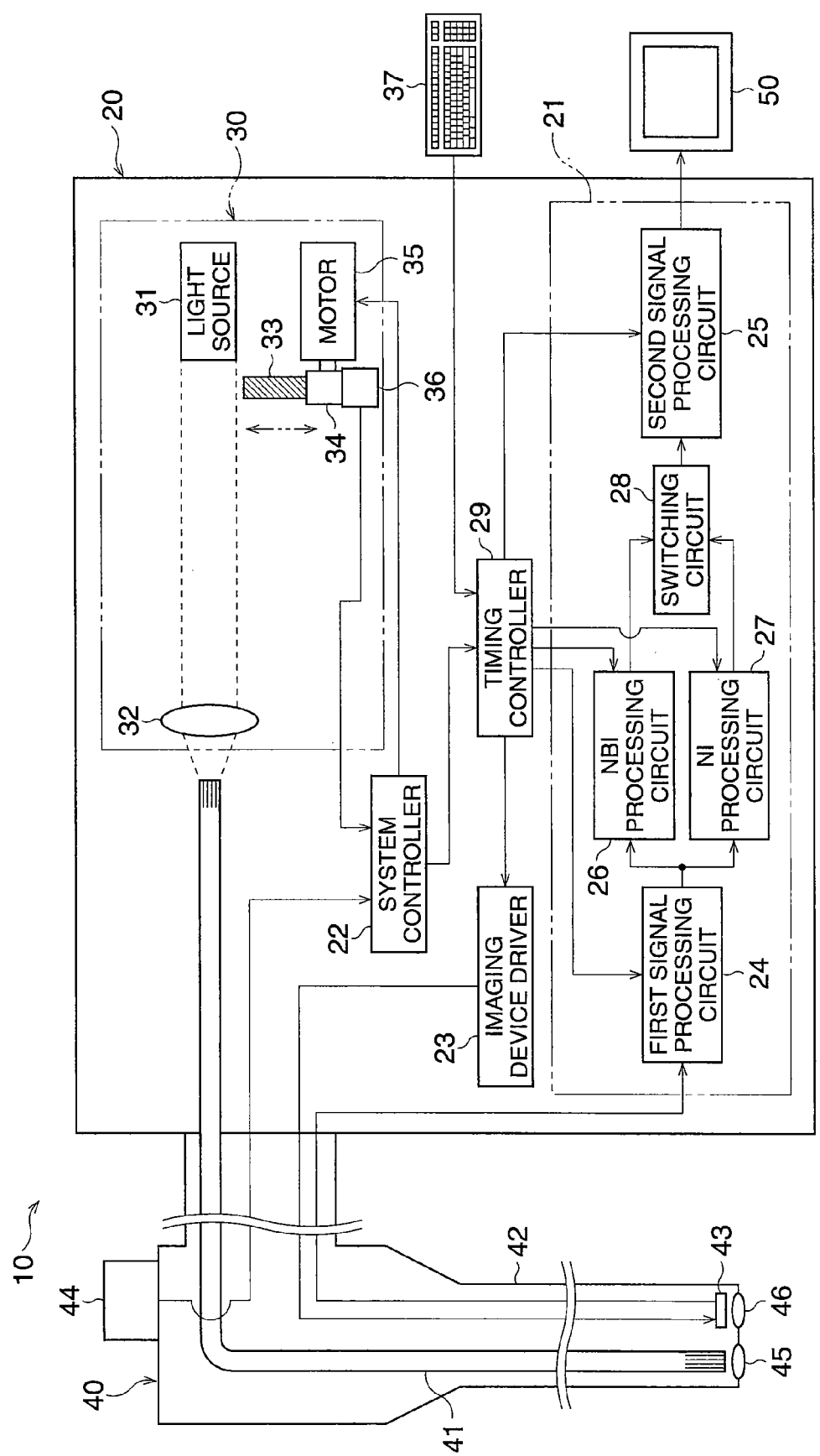
FIG. 1 is a block diagram showing the internal structure of an electronic endoscope system having an electronic endoscope, an endoscope light unit, and an endoscope processor of an embodiment of the present invention.

The present invention is described below with reference to the embodiment shown in the drawings.

In FIG. 1, an electronic endoscope system 10 comprises an endoscope processor 20, an electronic endoscope 40, and a monitor 50. The endoscope processor 20 is connected to the electronic endoscope 40 and the monitor 50. A light source unit 30 is housed in the endoscope processor 20. The light source unit 30 emits light for illuminating an object (not depicted). The light that is emitted from the light source unit 30 is irradiated onto the object via the light guide 41 housed in the electronic endoscope 40.

An imaging device 43, such as a CCD image sensor, is mounted in a head end of an insert tube 42 of the electronic endoscope 40. The imaging device 43 captures an optical image of the object. Then, the imaging device 43 generates an image signal corresponding to the captured optical image. The image signal is sent to the endoscope processor 20. An image signal processing unit 21 is mounted in the endoscope processor 20. The image signal processing unit 21 carries out predetermined signal processing for the image signal. The image signal, having undergone the predetermined signal processing, is sent to the monitor 50, and then the image is displayed on the monitor based on the sent image signal.

The light source unit 30 comprises a light source 31, a condenser lens 32, a light source filter 33, a filter driving mechanism 34, a motor 35, and a position detector 36. The light source 31 emits white light. The condenser lens 32 is mounted on the optical path from the light source 31 to the incident end of the light guide 41. The condenser lens 32 condenses the light for the incident end, and then the light is made incident on the incident end of the light guide 41.

The light source filter 33 is supported by the filter driving mechanism 34. The filter driving mechanism 34 can shift the light source filter 33, and the light source filter 33 can be inserted into the optical path or removed from the optical path. The shift of the light source filter 33 is performed by driving the motor 35. The motor 35 is controlled by a system controller 22.

The filter driving mechanism 34 is equipped with the position detector 36. The position detector 36 detects the position of the light source filter 33. The position of the light source filter 33 is transmitted as a signal from the position detector 36 to the system controller 22. The motor 35 is controlled by the system controller 22 based on the position of the light source filter 33.

Figure 2:
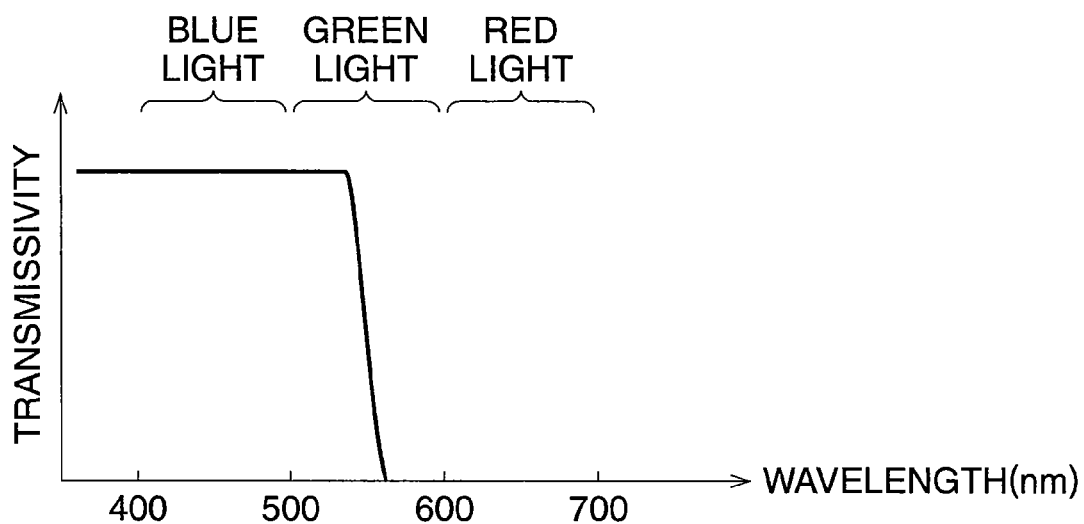
FIG. 2 illustrates a spectral characteristic of the light source filter.

As shown in FIG. 2, the light source filter 33 is formed of a material that shields the red light component and a part of the green light component, and allows another part of the green light component and the blue light component to penetrate. In particular, the material allows light components of wavelengths shorter than 550 nm to penetrate.

Accordingly, when the light source filter 33 is inserted into the optical path, a part of the green light component and the blue light component in white light is made incident on the incident end of the light guide 41. On the other hand, when the light source filter 33 is removed from the optical path, white light is made incident on the incident end of the light guide 41.

The insertion and the removal of the light source filter 33 are started by a user's operating the change switch 44 mounted in the electronic endoscope 40. The change switch 44 is connected to the system controller 22. The system controller 22 controls the motor to insert into or to remove the light source filter 33 from the optical path based on the user's operating the change switch 44.

The light emitted from the out end of the light guide illuminates a peripheral area near the head end of the insert tube 42 through a diffuser lens 45. An optical image of the illuminated object is captured by the imaging device 43 through an object lens 46. An imaging device driver 23 drives the imaging device 43 so that the imaging device 43 performs an image capturing operation, and then the imaging device 43 generates an image signal.

A plurality of pixels form a receiving surface of the imaging device 43. When the imaging device 43 performs the image capturing operation, each pixel generates a pixel signal in accordance with an amount of received light. The image signal comprises a plurality of pixel signals generated by a plurality of the pixels.

Figure 3:
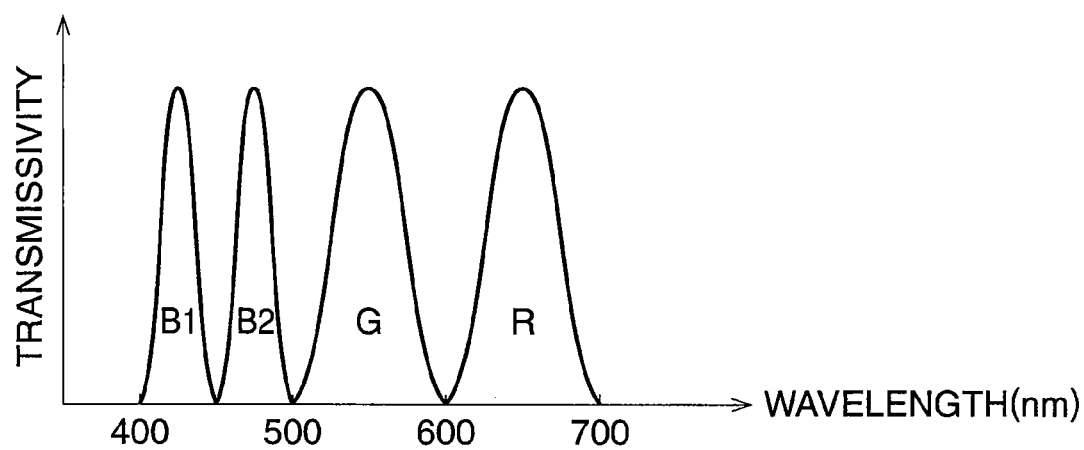
FIG. 3 illustrates spectral characteristics of color filters.

Each pixel is covered with one of a red color filter, a green color filter, a first blue color filter, or a second blue color filter. As shown in FIG. 3, the first blue color filter allows a blue light component, of which the wavelength is within a band of 400 nm~450 nm (see symbol B1), to penetrate. The second blue color filter allows a blue light component, of which the wavelength is within a band of 450 nm~500 nm (see symbol B2), to penetrate. The green color filter allows a green light component, of which the wavelength is within a band of 500 nm~600 nm (see symbol G), to penetrate. The red color filter allows a red light component, of which the wavelength is within a band of 600 nm~700 nm (see symbol R), to penetrate.

Figure 4:
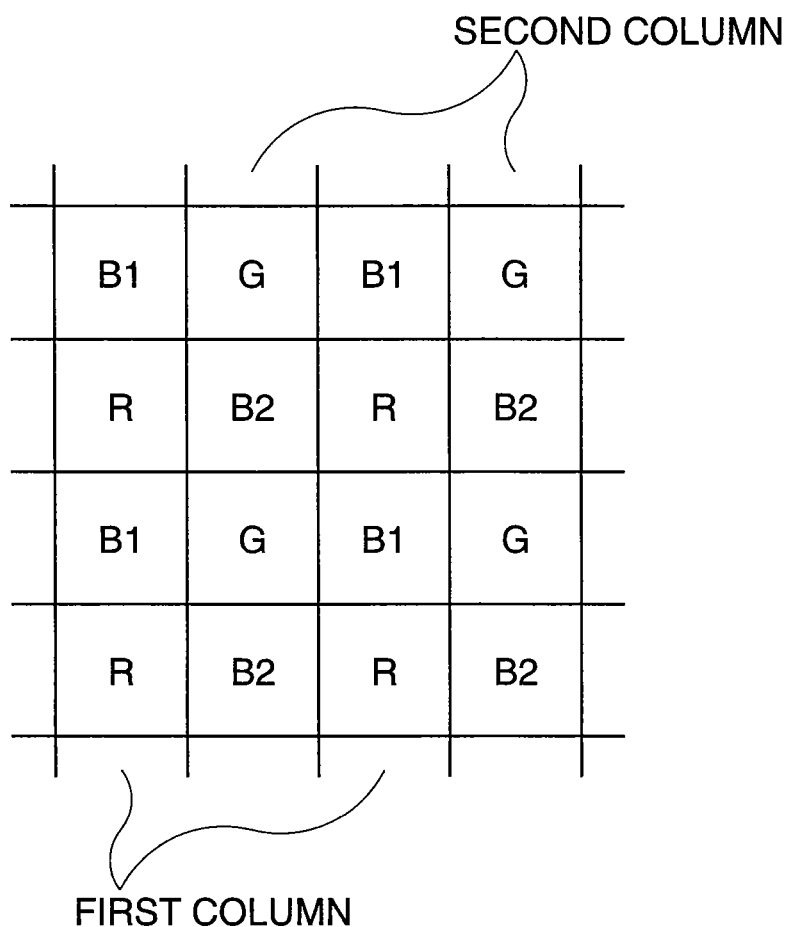
FIG. 4 illustrates the arrangement of the color filters on the receiving surface.

As shown in FIG. 4, the red color filter (see symbol R) and the first blue color filter (see symbol B1) are repeatedly and interleavingly arranged along a first column. The green color filter (see symbol G) and the second blue color filter (see symbol B2) are repeatedly and interleavingly arranged along a second column. The first and the second columns are arranged repeatedly and interleavingly. Incidentally, the second blue color filter is arranged in the same row as the red color filter, and the first blue color filter is arranged in the same row as the green color filter.

The pixel signal generated by each pixel covered with each color filter is a pixel signal in accordance with the amount of received color light component penetrating each color filter. Accordingly, a pixel covered with the red color filter generates the R signal component in accordance with the amount of received red light component. A pixel covered with the green color filter generates the G signal component in accordance with the amount of received green light component. A pixel covered with the first blue color filter generates the B1 signal component in accordance with the amount of received partial blue light component of one wavelength. A pixel covered with the second blue color filter generates the B2 signal component in accordance with the amount of received partial blue light component of a different wavelength. The R, G, B1, and B2 signal components are sent to the image signal processing unit 21.

Incidentally, when the light source filter 33 is inserted into the optical path, the signal intensity of the R signal component is substantially at zero level because the red light component is not irradiated onto an object at that time.

The image signal processing unit 21 comprises a first signal processing circuit 24, a second signal processing circuit 25, a narrow band image (hereinafter referred to as NBI) processing circuit 26, a normal image (hereinafter referred to as NI) processing circuit 27, and a switching circuit 28.

The image signal, comprising the R, G, B1, and B2 signal components, is sent to the first signal processing circuit 24. The first signal processing circuit 24 converts the image signal from an analog signal to a digital signal, and carries out predetermined signal processing.

The image signal, having undergone the predetermined signal processing, is sent to either the NBI processing circuit 26 or the NI processing circuit 27. The first signal processing circuit 24, the NBI processing circuit 26, and the NI processing circuit 27 are all connected to a timing controller 29. The timing controller 29 controls the signal processing of each of the first signal processing circuit 24, the NBI processing circuit 26, and the NI processing circuit 27. Further, the timing controller 29 determines whether the first signal processing circuit 24 sends the image signal to the NBI processing circuit 26, or to the NI processing circuit 27.

The timing controller 29 is connected to the system controller 22. The system controller 22 controls an operation of the timing controller 29. As for changing the circuit where the image signal is sent, the system controller 22 controls the timing controller 29 based on the input operation to the change switch 44, and then the circuit where the image signal is sent is determined.

The NI processing circuit 27 carries out predetermined signal processing, such as color separation processing, white balance processing, interpolation processing, gamma correction processing, and Y/C processing, for the image signal. Incidentally, the B1 and the B2 signal components are summed, and then a signal corresponding to the blue light component is generated. The predetermined signal processing is carried out with the generated signal corresponding to the blue light component.

In the summing computation of the B1 and the B2 signal components, the B1 and the B2 signal components can be weighted separately. The weights to multiply the B1 and the B2 signal components are modified according to a user's input operation at a control panel (not depicted) or a keyboard 37, which is connected to the timing controller 29.

On the other hand, the NBI processing circuit 26 carries out color separation processing, interpolation processing, and gamma correction processing for the image signal. After the gamma correction processing, the NBI processing circuit 26 carries out edge enhancement processing only for the B1 signal component. Further, the NBI processing circuit 26 carries out Y/C processing also for the B1 signal component (which has undergone the edge enhancement processing), the B2 signal component, and the G signal component. Incidentally, the NBI processing circuit 26 can amplify the B1 signal component that has undergone the edge enhancement processing, and then the amplified B1 signal component can be used for the Y/C processing, instead of an unamplified B1 signal component. A gain to amplify the B1 signal component can be modified according to a user's input operation at the control panel or the keyboard 37.

The image signal, for which the NI processing circuit 27 or the NBI processing circuit 26 has carried out the above signal processing, is sent to the switching circuit 28. The switching circuit 28 sends the image signal, output from either the NI processing circuit 27 or the NBI processing circuit 26, to the second signal processing circuit 25.

The second signal processing circuit 25 converts the sent image signal into a composite video signal. Further, the second signal processing circuit 25 carries out predetermined signal processing, such as D/A conversion processing, clamp processing, and blanking processing.

The composite video signal, having undergone the predetermined signal processing, is output to the monitor 50. Then, as described above, a captured object is displayed on the monitor 50. Incidentally, when white light is irradiated onto an object, an NI of the object is displayed based on the image signal for which the NI processing circuit 27 has carried out the above-mentioned signal processing. On the other hand, when blue-green light is irradiated onto an object by inserting the light source filter 33 into the optical path, an NBI of the object is displayed based on the image signal for which the NBI processing circuit 26 has carried out the above-mentioned signal processing. In the NBI, a tissue under an organ at a certain depth is emphasized.

Figure 5:
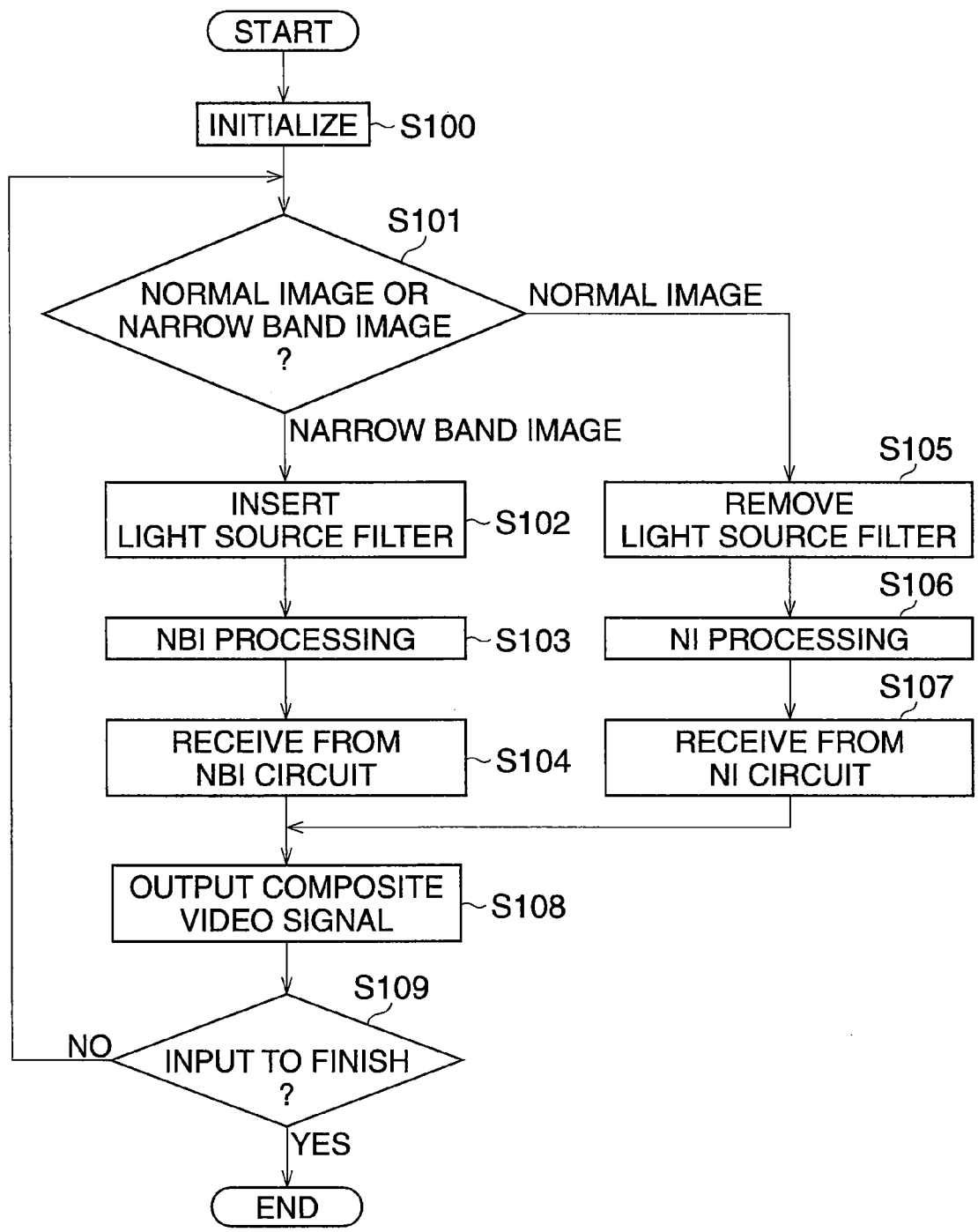
FIG. 5 is a flowchart describing the signal process carried out by an endoscope processor for displaying an NI or an NBI.
Figure 6:
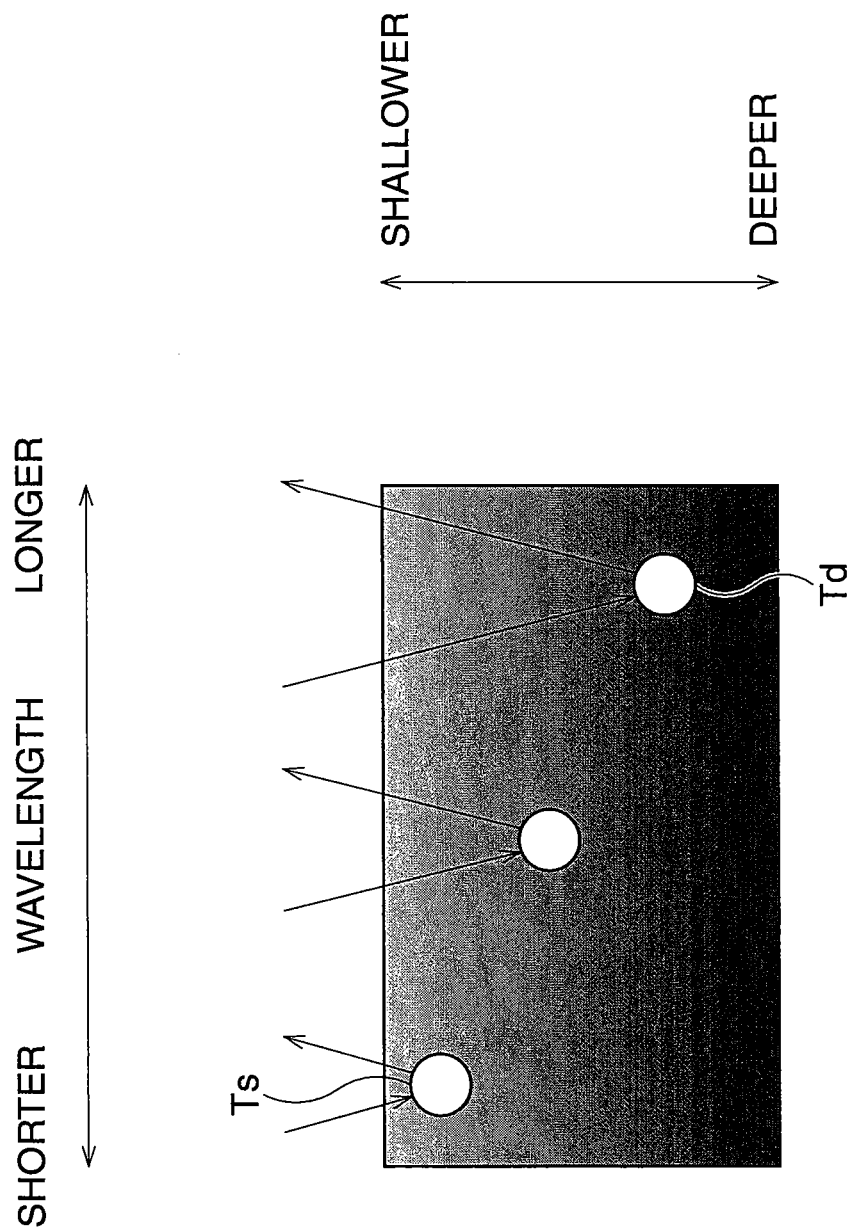
FIG. 6 illustrates a difference in depth for light of different wavelength to reach under an organ wall.

Next, signal processing for displaying an NI or an NBI carried out by the endoscope processor 20 is explained below using the flowchart of FIG. 5.

At step S100, the entire endoscope system is initialized. In the initialization, the imaging device 43 is enabled to capture an optical image, the light source 31 emits white light, and the image signal processing unit 21 is enabled to carry out the signal processing mentioned above.

After the initialization, the process proceeds to step S101. At step S101, it is determined whether the change switch 44 is switched to the NI display mode or to the NBI display mode.

If the change switch 44 is switched to the NBI display mode, the process proceeds to step S102. At step S102, the light source filter 33 is inserted into the optical path. Then, the process proceeds to step S103. At step S103, the image signal generated by the imaging device 43 is sent to the NBI processing circuit 26, and then NBI processing is carried out for the sent image signal. The NBI processing is the signal processing carried out by the NBI processing circuit 26, including the edge enhancement processing only for the B1 signal component.

After NBI processing, the process proceeds to step S104. At step S104, the switching circuit 28 switches to the NBI processing circuit 26 to display the NBI.

At step S101, if the change switch 44 is switched to the NI display mode, the process proceeds to step S105. At step S105, the light source filter 33 is removed from the optical path of the light emitted from the light source 31, and then the process proceeds to step S106. At step S106, the image signal generated by the imaging device 43 is sent to the NI processing circuit 27, and then NI processing is carried out for the sent image signal. NI processing is the signal processing carried out by the NI processing circuit 27.

After NI processing, the process proceeds to step S107. At step S107, the switching circuit 28 switches to the NI processing circuit 27 to display the NI.

After steps S104 or S107, the process proceeds to step S108. At step S108, the composite video signal is generated based on the image signal (which has undergone the NBI processing or the NI processing), and then, the composite video signal is sent to the monitor 50.

At step S109, it is determined whether there is an input command to finish the observation by the electronic endoscope 40. If there is an input command to finish, then processing for displaying the image finishes; otherwise, the process returns to step S101. The processes from step S101 to step S109 are repeated until there is an input command to finish.

In the above embodiment, a specified tissue under an organ can be clearly observed without a rotating color filter in the field sequential image pickup system. Since not a field sequential image pickup system, but a 1-chip image pickup system, is applied to the electronic endoscope system 10, a high-quality image can be displayed, resulting in enabling a more precise diagnosis. In addition, since the entire mechanism of the electronic endoscope system 10 is simpler than that of an endoscope system applying a field sequential image pickup system, it is possible to simplify the entire mechanism and to carry out maintenance relatively easily.

Each function of the electronic endoscope 40, the light unit 30, and the endoscope processor 20, forming the electronic endoscope system 10, is described in detail as follows:

First, the function of the electronic endoscope 40 is described below.

The electronic endoscope 40 in the above embodiment can generate an image signal corresponding to an NBI, even if white light is irradiated onto an object. The reason is that a pixel signal, in accordance with an amount of a received light component of a specified band that reaches a desired depth under an organ, can be generated with part of the pixels that are covered with a color filter that the light component of the specified band penetrates.

In particular, the electronic endoscope 40 can generate a pixel signal in accordance with the amount of a received light component, of which the wavelength is within a band of 400 nm~500 nm. The light component, of which the wavelength is within a band of 400 nm~500 nm, reaches the depth where there is a capillary under an organ. Accordingly, the image of a capillary that is an important target to observe can be displayed in detail.

In addition, a pixel signal covered with the first blue color filter can generate a pixel signal in accordance with the amount of a received light component of which the wavelength is about 420 nm. The light component, of which the wavelength is about 420 nm, is maximally absorbed by hemoglobin. Accordingly, the image of the capillary can be displayed in more detail. In addition, the image of a bleeding area can be displayed clearly and conspicuously.

Further, the electronic endoscope 40 in the above embodiment can generate not only an image signal corresponding to an NBI, but also an image signal corresponding to an NI, accurately. For displaying an NBI, only either the first or the second blue color filter is used for an imaging device. On the other hand, an NI cannot be accurately displayed by such an imaging device, because the blue light component of an object irradiated by white light cannot be captured completely only by generating a pixel signal in accordance with the received light that penetrates the first or second blue color filter. However, as described above, the electronic endoscope 40 can generate image signals corresponding to an accurate NI also, because the blue light component can be detected by summing pixel signals generated by pixels separately covered by the first and the second blue filters.

Further, four pixels arranged in two rows and two columns are separately covered with the red color filter, the green color filter, or the first and the second blue color filter in the electronic endoscope 40 of the above embodiment. Accordingly, an image, of which the resolutions along a column direction and a row direction are identical to each other, can be displayed.

Incidentally, the first blue filter, which passes a band of light in the range of 400 nm~450 nm for capturing a capillary located in shallow depth under an organ, and the second blue filter, which passes a band of light in the range of 450 nm~500 nm, are used in the electronic endoscope 40 of the above embodiment. However, any filter that only specified light penetrates may be used, as long as the specified light reaches the depth where a tissue to be observed is located under an organ.

Further, it is possible to generate the B1 or the B2 signal component for displaying an NBI corresponding to the blue light component in the electronic endoscope 40 of the above embodiment. However, a red or a green signal component, corresponding to the red or the green light component of a narrow band wavelength, may be generated by covering some pixels with a red or green color filter that only the red or green light component of the narrow band wavelength penetrates.

Second, the function of the light source unit 30 is described below.

Tissue at a shallow depth under an organ may be observed by detecting the blue light component of reflected light for an object in the above embodiment. The sensitivity of the imaging device 43, such as a CCD, for the blue light component is lower than that for the red or green light components. Accordingly, a higher amount of light irradiating an object is preferable for generating an image signal corresponding to an NBI of a blue light component. On the other hand, a lower amount of light irradiating an object is preferable for preventing the organ, which the light irradiates, from becoming damaged, such as by a burn. The light source unit 30 in the above embodiment can emit light from which the red light component that is mainly responsible for causing an organ's burn is excluded. In this way, an organ's burn may be prevented, even if a higher amount of light is emitted by the light source 31 for displaying a clear NBI.

The composite video signal corresponding to an NBI is generated based on not only the B1 and B2 signal components, but also on the G signal component by the endoscope processor 20, as described in detail later. However, in the prior art, it was difficult to generate B1 and B2 signal components, of which the signal intensity was high enough to display a clear NBI, without saturating the G signal component. The reason was that the amount of received blue light component at the imaging device was lower than that of the green light component when white light was irradiated onto an organ. To deal with the above problem, a part of the green light component from white light emitted by the light source 31 is shielded in the light source unit 30. Accordingly, the light source unit 30 can emit B1, B2, and G signal components, of which the light amount is nearly equal, resulting in generating B1 and B2 signal components for which the signal intensity is high without saturating the G signal component.

The light component for which the wavelength is shorter than 550 nm penetrates the light source filter 33 in the light source unit 30 of the above embodiment. However, any optical filters that enable the imaging device 43 to generate the B1, B2, and G signal components for which the signal intensities are nearly equal may be adaptable.

Third, the function of the endoscope processor 20 is described below.

An NBI colored by a single color is displayed by an electronic endoscope system 10 in the prior art because an image of an object irradiated only by light of a narrow band is displayed as an NBI. On the other hand, the endoscope processor 20 in the above embodiment generates an image signal corresponding to an NBI based on pixel signals in accordance with not only amounts of the received light component of the narrow band, but also with amounts of another received light component. Accordingly, the endoscope processor 20 enables a more vivid NBI to be displayed than that of an endoscope processor in the prior art.

On the other hand, if pixel signals in accordance with amounts of received light components of a predetermined narrow band and another band are used simultaneously for displaying an NBI, a tissue that a user desires to observe may not be clearly displayed by an endoscope system in the prior art because of different sensitivities of an imaging device. In particular, the sensitivity of the blue light component is lower than those of the red and the green light components. Accordingly, a tissue that mainly reflects the blue light component is invisible in the entire NBI. An image signal corresponding to an NBI is generated with the B1 signal component, for which the edge enhancement process is carried out, and other signal components in the endoscope processor 20 of the above embodiment. In this way, an NBI based on a number of other primary color signal components can be displayed while showing the tissue, for example, that of a capillary, clearly and conspicuously.

The endoscope processor 20 in the above embodiment generates an image signal corresponding to the blue light component based on the B1 and B2 signal components. Accordingly, an NI as well as an NBI can be displayed accurately on the monitor 50.

The weights to multiply the B1 and the B2 signal components can be changed in the endoscope processor 20 of the above embodiment. Accordingly, an NI with improved color tone may be displayed on the monitor 50.

The endoscope processor 20 in the above embodiment carries out Y/C processing for the B1 signal component (which has undergone the edge enhancement processing), the B2 signal component, and the G signal component in the NBI processing circuit 26. However, the Y/C processing may be carried out for the R signal component in addition to the above color signal components. The signal intensity of the R signal component is substantially zero when the light source filter 33 is inserted into the optical path in the NBI display mode, so the R signal component may be excluded in carrying out Y/C processing in the NBI processing circuit 26 for a quick computation. If white light is irradiated onto an object without using the light source unit 30 and the signal intensity of the R signal component exceeds zero, it is preferable to use the R signal component also for the Y/C processing.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Applications Nos. 2005-237392 (filed on Aug. 18, 2005) and 2005-239946 (filed on Aug. 22, 2005), which are expressly incorporated herein, by reference, in their entirety.

The invention claimed is:

1. An electronic endoscope system, comprising:
an electronic endoscope including an imaging device having a first pixel covered with a first color filter penetrated by a first light component that reaches a predetermined depth, according to the location of an object to be observed, under an organ, wherein said first light component comprises one of three primary colors, and said imaging device has a second pixel covered with a second color filter penetrated by a second light component that contains the same primary color as the primary color of said first light component, a wavelength band of the second light component is different than a wavelength band of said first light component, a third pixel covered with a third color filter penetrated by a third light component that contains a different primary color than the primary color of said first light component, and a fourth pixel covered with a fourth color filter penetrated by a fourth light component that contains a different primary color than the primary colors of said first and said third light components, the electronic endoscope further comprising:

a light source that emits illumination light to illuminate an object;

a light source filter that shields a light component within a predetermined wavelength band from said illumination light; and a filter driver that inserts said light source filter into an optical path of said illumination light, or that removes said light source filter from said optical path.

2. An endoscope light unit according to claim 1, wherein a blue or green light component can penetrate said light source filter.

3. An endoscope light unit according to claim 1, wherein a light component, having a wavelength that is shorter than 550 nm, can penetrate said light source filter.

4. An electronic endoscope system, comprising:

an imaging device having a first pixel covered with a first color filter penetrated by a first light component that reaches a depth predetermined according to a location of an object to be observed under an organ; a second pixel covered with a second color filter penetrated by a second light component that contains the same color as a color of said first light component, a wavelength band of the second light component is different from a wavelength band of said first light component; a third pixel covered with a third color filter penetrated by a third light component that is a light component having a different color than the color of said first light component; and a fourth pixel covered with a fourth color filter penetrated by a fourth light component that is a light component having a different color than the colors of said first and said third light components;

an input that detects an input of a user for selecting one of a number of predetermined display modes to display an image captured by said imaging device;

a signal processor that carries out edge enhancement processing only for a pixel signal generated by said first pixel when a narrow band image display mode, which is one of said predetermined display modes, is selected;

a light source that emits illumination light to illuminate an object;

a light source filter that shields said fourth light component and a part of said third light component from said illumination light; and a filter driver that inserts said light source filter into an optical path of said illumination light when said narrow band image display mode is selected.

5. The electronic endoscope system according to claim 1, further comprising a processor configured to enable selection of one of a predetermined number of image display modes for displaying an image captured by the electronic endoscope, said plurality of image display modes including at least a narrow band image display mode and a normal image display mode, said filter driver inserting said light source filter into the optical path of the illumination light when the narrow band image display mode is selected and removing said light source filter from said optical path of the illumination light when the normal image display mode is selected.

6. The electronic endoscope system according to claim 5, further comprising a processor configured to enable selection of one of a predetermined number of image display modes for displaying an image captured by the electronic endoscope, said plurality of image display modes including at least a narrow band image display mode and a normal image display mode, said filter driver inserting said light source filter into the optical path of the illumination light when the narrow band image display mode is selected and removing said light source filter from said optical path of the illumination light when the normal image display mode is selected.

7. An electronic endoscope according to claim 5, wherein said imaging device has a first series formed by said first and said third pixels arranged repeatedly and interleavingly along a first direction, and a second series formed by said second and said fourth pixel arranged repeatedly and interleavingly along said first direction, and said first and second series are arranged repeatedly and interleavingly along a second direction perpendicular to said first direction on a receiving surface of said imaging device.

8. An electronic endoscope according to claim 5, wherein the wavelength band of said first light component is within a range of between 400 nm and 450 nm.

9. An electronic endoscope according to claim 5, wherein wavelength bands of said second, said third, and said fourth light components are within ranges of between 450 nm and 500 nm, 500 nm and 600 nm, and 600 nm and 700 nm, respectively.

10. An endoscope light unit according to claim 5, wherein a blue or green light component can penetrate said light source filter.

11. An endoscope light unit according to claim 5, wherein a light component, having a wavelength that is shorter than 550 nm, can penetrate said light source filter.

* * * * *